United States Patent [19]

Materia et al.

[11] 4,241,188
[45] Dec. 23, 1980

[54] CULTURE BOTTLE HAVING STOPPER LOCK

[75] Inventors: Peter Materia, Wood-Ridge; Jayraj S. Desai, Closter, both of N.J.

[73] Assignee: Becton, Dickinson and Company, Paramus, N.J.

[21] Appl. No.: 82,616

[22] Filed: Oct. 9, 1979

[51] Int. Cl.³ ............................................. C12M 1/24
[52] U.S. Cl. ................................. 435/296; 215/260; 215/277; 435/317; 422/102
[58] Field of Search .............. 215/260, 274, 277, 280, 215/294, 307; 435/296, 287, 317; 422/102

[56] References Cited

U.S. PATENT DOCUMENTS

| | | | |
|---|---|---|---|
| 2,347,150 | 4/1944 | Consolazio | 215/260 X |
| 2,834,496 | 5/1958 | Boston et al. | 215/260 X |
| 2,884,151 | 4/1959 | Biederman | 215/307 X |
| 3,203,572 | 8/1965 | Scott, Jr. et al. | 215/260 |
| 4,176,756 | 12/1979 | Gellman | 215/274 |

Primary Examiner—Robert J. Warden

[57] ABSTRACT

An assembly is provided for the culturing of aerogenic microorganisms. It includes a culture bottle having a neck portion defining an opening therein. A lip is provided near the bottle opening and a stopper is positioned within the opening. A stopper lock is mounted on the bottle neck to prevent the stopper from blowing off due to pressure generated within the bottle. The lock is capable of limited movement along the neck, however, to allow the stopper to rise to a height which allows venting of the bottle. The stopper lock includes an inwardly extending upper flange, an inwardly extending lower flange, and sidewalls interconnecting the flanges. The upper flange is capable of engaging the upper surface of the stopper while the lower flange is capable of engaging the lower surface of the lip. The stopper lock is movable along the neck between positions of engagement with the upper surface of the stopper and the lower surface of the lip.

8 Claims, 6 Drawing Figures

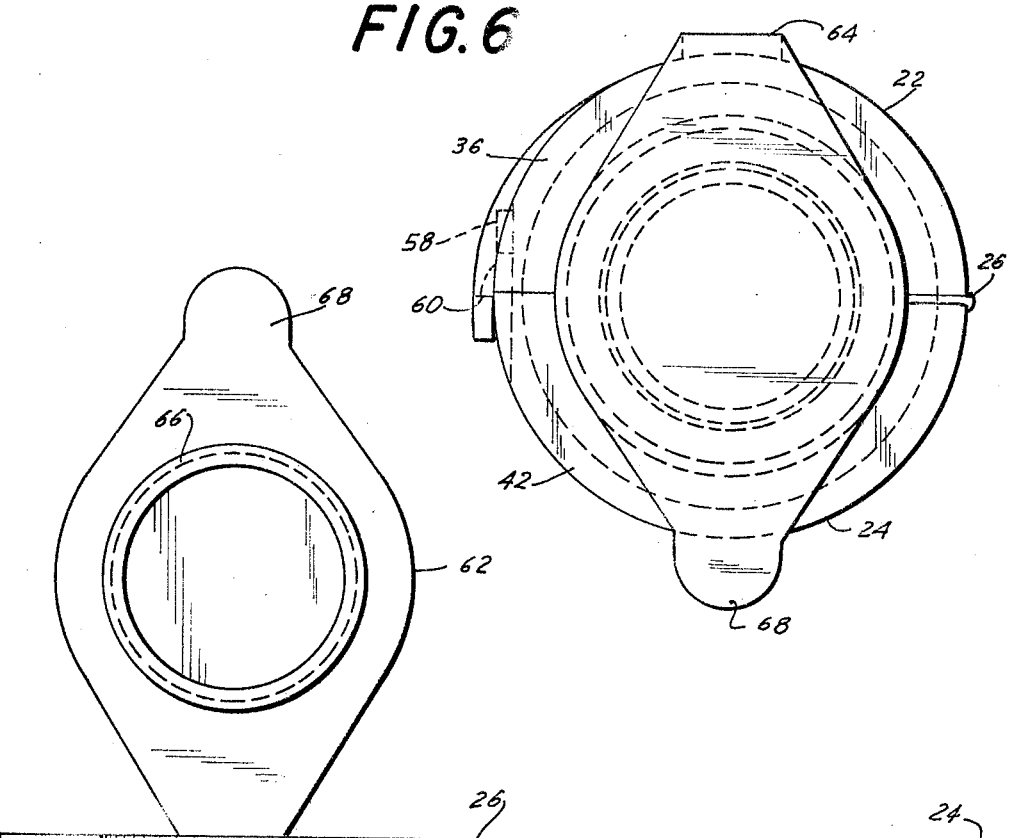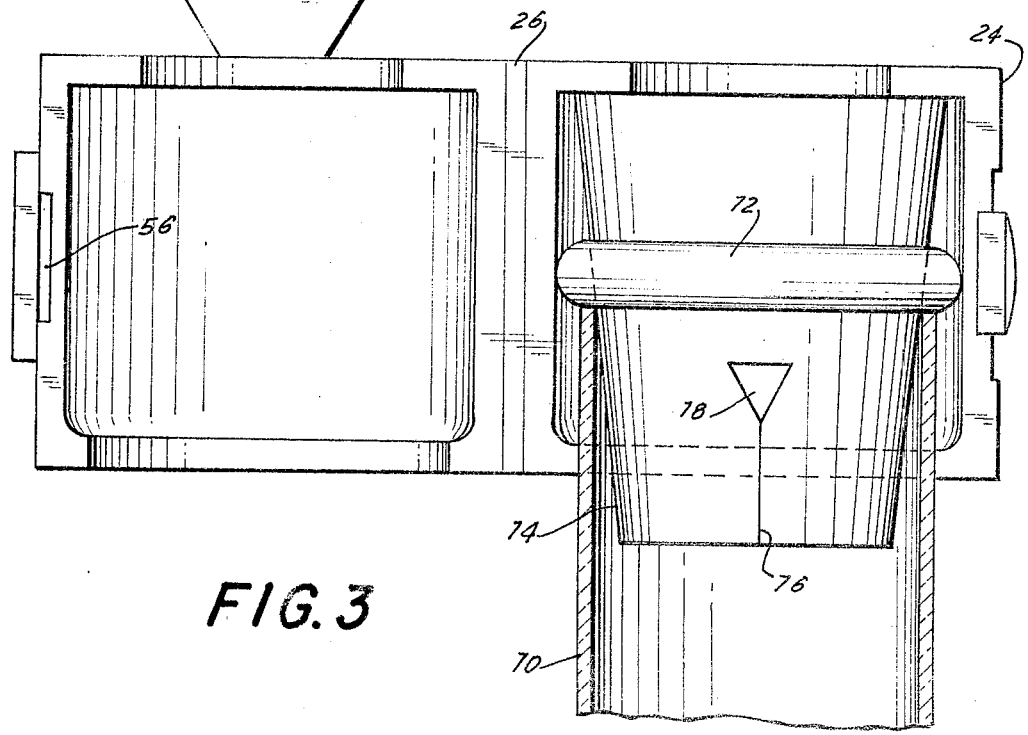

CULTURE BOTTLE HAVING STOPPER LOCK

BACKGROUND OF THE INVENTION

The field of the invention relates to stopper locks for culture bottles.

Culture bottles are commonly utilized for allowing the growth of microorganisms within a liquid medium. The bottle can either be retained in a sealed condition through the use of a stopper or vented through the stopper. If the stopper is not vented, the presence of (gas producing) aerogenic bacteria within the bottle can result in a significant force due to gas pressure applied against the stopper. To prevent the stopper from blowing off, a stopper lock may be employed.

SUMMARY OF THE INVENTION

The invention is directed to a stopper lock which allows a stopper within a culture bottle to move a limited distance out of the bottle when the pressure reaches certain levels. The stopper is constructed such that when it moves said limited distance, the interior of the bottle will be vented to the atmosphere.

The stopper lock is integrally formed from a polymeric material such as polypropylene. It includes an upper flange extending inwardly to provide an aperture of lesser diameter than the open end of the bottle, a lower inwardly extending flange capable of engaging a lip on the neck of the bottle, a hinge along one side of the body of the lock, and fastening means on the opposite side of the lock. The hinge and fastener divide the stopper lock into two halves which may easily be applied to the bottle and locked thereon. A hinged closure may also be employed to cover the aperture defined by the upper flange.

The stopper utilized may be formed with a slit therein so that when it is raised to a certain point, the interior of the bottle may be vented therethrough.

The bottle, stopper and stopper lock are assembled so that venting occurs when the stopper is forced a certain distance out of the bottle neck. The stopper lock prevents the stopper from being entirely ejected. The flanges on the stopper lock are so arranged that the stopper may only rise to a certain height before the lower flange engages the lower portion of an annular protruding portion or lip of the bottle. Further movement is impossible. The stopper is constructed so as to vent the interior of the bottle to the atmosphere when at this height.

Venting is possible as the engagement of the lower flange and bottle lip do not provide a fluid-tight seal.

BRIEF DESCRIPTION OF THE DRAWINGS

FIG. 3 is a side elevation view of the stopper lock being applied to a culture bottle;

FIG. 6 is a top view of a culture bottle having a stopper lock thereon.

DESCRIPTION OF THE INVENTION

The present invention is an improvement of the commonly assigned application of Barry N. Gellman filed June 27, 1977 under Ser. No. 809,972 now U.S. Pat. No. 4,176,756.

Figure 1:
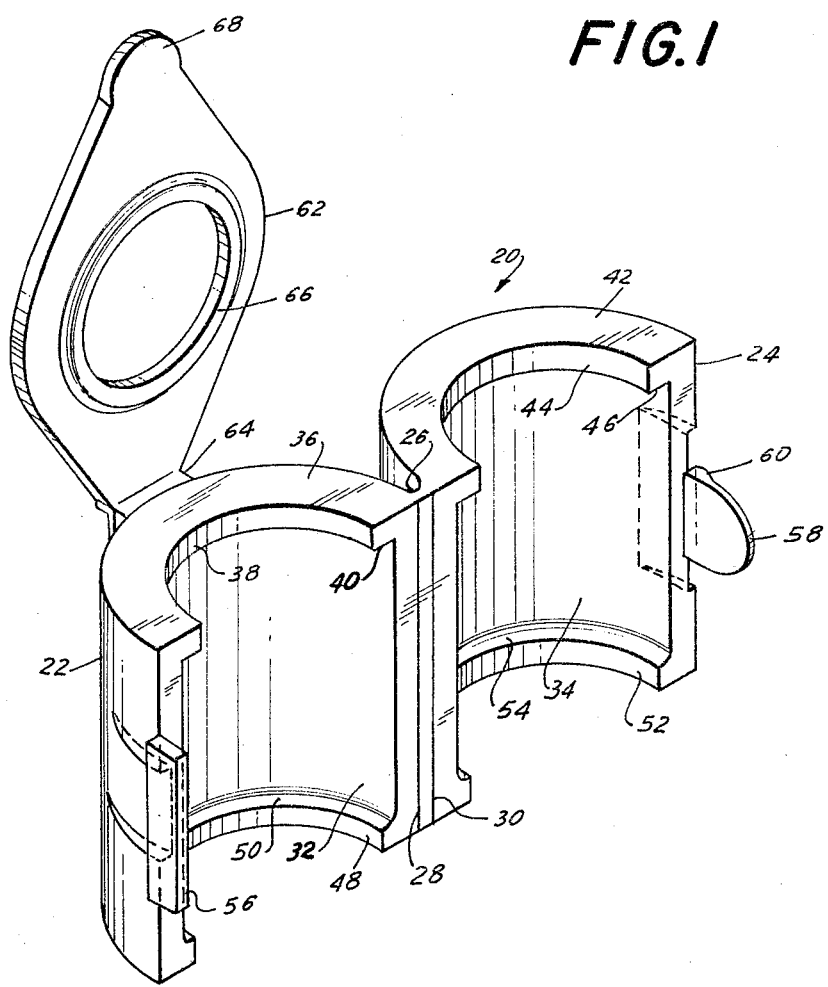
FIG. 1 is a perspective view of the stopper lock prior to application to a culture bottle.
Figure 2:
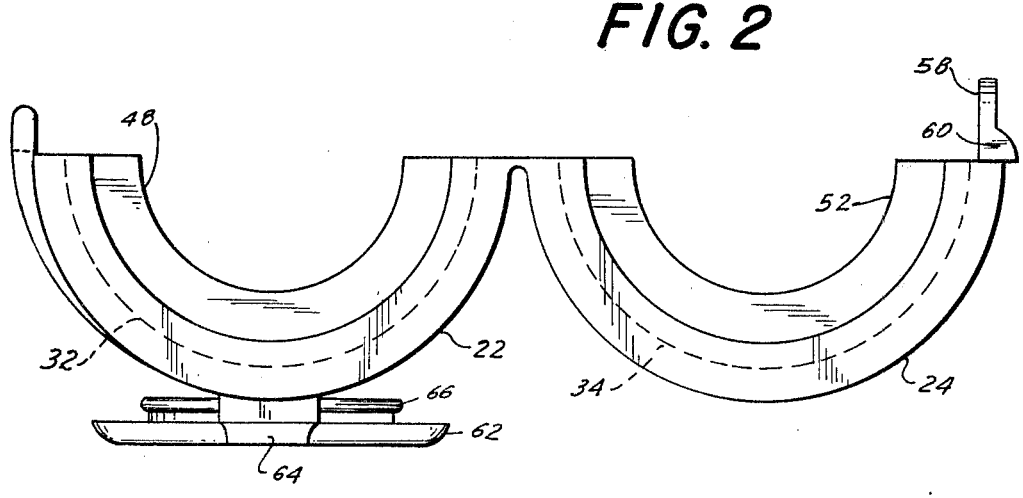
FIG. 2 is a bottom view of the stopper lock shown in FIG. 1.

The stopper lock 20 utilized within the invention is shown in FIGS. 1 and 2 in the unlocked condition. It includes a first lock half 22 and a second lock half 24 hinged together along a commonly joined area 26. The halves are integrally molded as a one piece unit and can be formed of a conventional plastic material such as polypropylene. The hinge 26 is formed by providing an integral "living hinge" portion including fold lines 28 and 30 in the molding process which facilitates the rotation of mold halves 22 and 24 into alignment with one another to form the complete lock 20.

Each lock half includes a central semi-cylindrical portion with lock half 22 including central portion 32 and lock half 24 including central portion 34.

The upper portion of lock half 22 includes an inwardly extending arcuate flange 36 with a central aperture 38 therein. The flange 36 forms a shoulder 40 on its bottom surface for engagement with the top of a stopper of a culture bottle. Similarly, lock half 24 includes an inwardly extending arcuate flange 42 with a central aperture 44, the flange 42 forming an inwardly extending shoulder 46 with its bottom surface. As can be seen, when the lock halves are rotated into engagement with one another, the flanges 36 and 42 form an inwardly extending circular wall with a circular aperture formed by openings 38 and 44. The bottom surfaces 40 and 46 of the flanges are adapted to abut the upper surface of the stopper.

The lower portion of lock half 22 includes a second inwardly extending arcuate flange 48. The flange 48 forms a shoulder 50 on its upper surface for engagement with the bottom surface of a lip on a culture bottle. Similarly, lock half 24 includes a second inwardly extending flange 52 at its bottom. This flange 52 also forms a shoulder 54 on its upper surface.

A fastening means is provided for coupling halves 22 and 24. Lock half 22 includes a slot 56 adapted to receive a projection 58 on lock half 24. The projection 58 includes a shoulder 60 which snaps behind the walls defining the slot. A complete description of the fastening means is found in the above-mentioned Ser. No. 809,972.

Lock half 22 includes a cover 62 which is integrally formed thereon. A hinge 64 connects the cover with the body portion of the lock half. The cover has a downwardly projecting ring 66 on its bottom surface which is adapted to snap within the circular aperture formed by openings 38 and 44. The end 68 of the cover is elongated so that it projects beyond the walls defining the outer circumference of the lock rest. This facilitates the opening of the cover.

The stopper lock 20 is applied to the neck of a culture bottle 70 as shown in FIG. 3. The neck includes a lip 72 defining an upper opening therein. A resilient stopper 74 is sealingly inserted within the bottle opening. The stopper bottom is divided into two semi-cylindrical sections by a slit 76 which widens into a V-shaped portion 78. These features allow the simple insertion of the stopper into the bottle.

Figure 4:
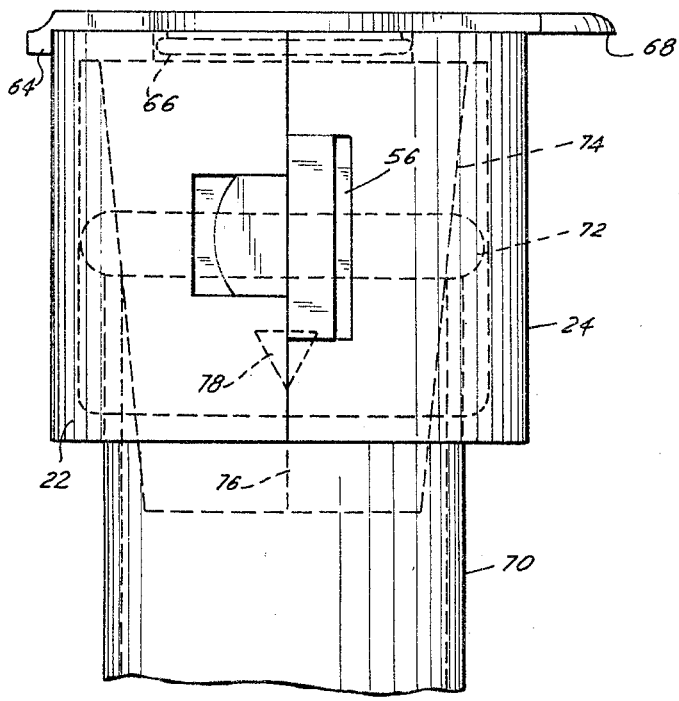
FIG. 4 is a side elevation view of a culture bottle having a fully inserted stopper.

The two lock halves 22 and 24 are then coupled by snapping the shoulder of the projection 58 behind the slot 56. The bottom surface 40 of the upper flange rests upon the upper surface of the stopper 74 as shown in FIG. 4.

If the culture bottle is used for culturing aerogenic bacteria, pressure will increase within the bottle as bacterial growth progresses. Internal pressures of 65 psig or more may be generated. When such high pressures occur, it is desirable to prevent the stopper from blowing off. However, the stopper should be allowed to rise to a height which allows venting of the bottle. With this object in mind, the distance between the upper flanges 36, 42 and the lower flanges 48, 52 is sufficient to allow the stopper to rise to at least a height at which the bottle vents. The necessary distance between flanges is, of course, dependent upon the height of the stopper and the location of the lip on the bottle.

Figure 5:
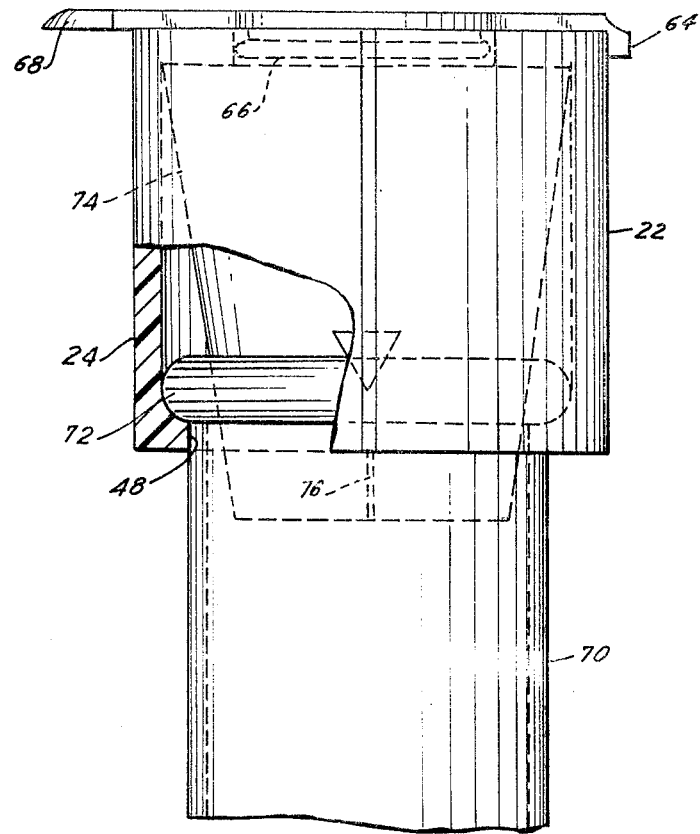
FIG. 5 is a side elevation view of a culture bottle in which the stopper has risen to a height to allow venting.

FIG. 5 illustrates the positions of the stopper and retaining lock after a sufficient amount of pressure has caused the stopper to rise. A fluid-tight seal is normally formed between the walls of the stopper and bottle before the growth of microorganisms occurs. Once the stopper rises a certain distance, however, it will sit rather loosely on the lip defining the bottle opening. Gas may accordingly exit from the bottle between the walls of the stopper and the lip. If the slit 76 or V-shaped area 78 rises above the bottle lip, gas may also exit through them. The stopper lock 20 does not form a fluid-tight seal with the bottle so the generated gas may enter the atmosphere.

To prevent the stopper from blowing off, the shoulders 50 and 54 engage the bottom of the lip 72 if the stopper rises to a certain level. The upper flanges 38, 44 of the stopper lock engage the top of the stopper. The stopper can be resealed by pushing the stopper lock down.

It will be appreciated that the invention may be applied in conjunction with stoppers and culture bottles of various designs. The flanges may be arranged to allow the desired degree of stopper movement regardless of the position of the bottle lip or the length of the stopper extending from the bottle. The foregoing specification is accordingly intended to be illustrative rather than limiting, and the scope of the invention is to be determined by the appended claims.

What is claimed is:

1. An assembly for the culturing of microorganisms, comprising:
   a culture bottle having a neck portion defining an opening therein;
   an annular protruding portion extending radially from said neck;
   a stopper positioned within said opening; and
   a stopper lock movably mounted on said bottle neck, said stopper lock including an inwardly extending upper flange, an inwardly extending lower flange, and side walls interconnecting said flanges, the upper flange capable of engaging the upper surface of said stopper, the lower flange capable of engaging the lower surface of said annular protruding portion, there being a sufficient distance between said upper and lower flanges to allow said stopper to rise to a height from said opening to allow the venting of the interior of the bottle, the stopper lock being movable along said neck between position of engagement with the upper surface of the stopper and the lower surface of the protruding portion.

2. An assembly as described in claim 1 wherein said stopper lock comprises a pair of semi-cylindrical halves coupled by fastening means.

3. An assembly as described in claim 2 wherein said upper flange provides an aperture of lesser diameter than the upper surface of the stopper and the lower flange provides an aperture of lesser diameter than said annular protruding portion.

4. An assembly as described in claim 3 further including a cover hingedly secured to said stopper lock and having a portion adapted to snap within said aperture provided by said upper flange.

5. An assembly as described in claim 3 wherein said annular protruding portion is a lip defining the opening in the neck of the bottle.

6. An assembly as described in claim 1 wherein said stopper includes venting means extending from a lower portion thereof for a sufficient distance towards the upper surface of said stopper such that when said stopper rises to a certain height from said opening, the bottle is vented through said venting means.

7. An assembly as described in claim 6 wherein said venting means comprises a slitted stopper bottom defining two semi-cylindrical sections therein.

8. An assembly as described in claim 1 wherein said stopper lock is an integrally molded polymeric structure.

* * * * *